United States Patent [19]

Seemuth

[11] Patent Number: 4,459,419

[45] Date of Patent: Jul. 10, 1984

[54] HYDROGENATION PROCESS USING CATIONIC RUTHENIUM-CONTAINING ZEOLITE

[75] Inventor: Paul D. Seemuth, Oak Park, Mich.

[73] Assignee: Ethyl Corporation, Richmond, Va.

[21] Appl. No.: 414,477

[22] Filed: Sep. 2, 1982

[51] Int. Cl.³ .................. C07D 307/08; C07D 307/12
[52] U.S. Cl. .................... 549/429; 260/690;
546/164; 549/356; 549/497; 549/502; 568/831;
568/832; 568/881; 585/350; 585/700
[58] Field of Search ............... 260/690; 549/429, 356,
549/497, 502; 568/831, 832, 881; 546/164;
585/350, 700

[56] References Cited

U.S. PATENT DOCUMENTS

| | | | |
|---|---|---|---|
| 3,269,934 | 8/1966 | Hansford | 208/111 |
| 3,339,451 | 3/1966 | Young | 208/111 |
| 3,364,135 | 1/1968 | Hansford | 208/120 |
| 3,375,205 | 3/1968 | Wadlinger et al. | 252/455 |
| 3,459,676 | 8/1969 | Kerr | 252/430 |
| 3,476,821 | 11/1969 | Brandenburg et al. | 260/672 |
| 3,524,809 | 8/1970 | Hansford | 208/111 |
| 3,600,301 | 8/1971 | Rausch | 208/111 |
| 3,647,681 | 9/1969 | Egan | 208/111 |
| 3,647,682 | 3/1972 | Rabo et al. | 208/120 |
| 3,963,788 | 6/1976 | Kruse et al. | 260/635 |
| 3,963,789 | 6/1976 | Kruse et al. | 260/635 |

OTHER PUBLICATIONS

B. Coughlan et al., J. of Catalysts, 49, pp. 97–108 (1977).
I. R. Leith, Chemsa (May 1978) "Hydrogenation and Fischer-Tropsch Synthesis on Zeolite Group VIII Metal Catalysts".
H. Arai et al., J. of Catalysts, 75 pp. 188–189 (May 1982).

*Primary Examiner*—Richard Raymond
*Attorney, Agent, or Firm*—Donald L. Johnson; John F. Sieberth; Joseph D. Odenweller

[57] ABSTRACT

Zeolite-ruthenium catalysts in which the ruthenium is in the form of a cation are very effective in catalyzing the hydrogenation of a broad range of organic compounds.

5 Claims, No Drawings

HYDROGENATION PROCESS USING CATIONIC RUTHENIUM-CONTAINING ZEOLITE

BACKGROUND

Zeolite supported ruthenium catalysts are known (Coughlin et al, *J. of Catalysts*, 49, pp. 97–108, 1977). The ruthenium is reduced to the free-metal state by contacting with $H_2$ for six hours at 713° K. prior to use as a hydrogenation catalyst.

Kruse et al U.S. Pat. No. 3,963,788 reports the hydrogenation of carbohydrate using a zeolite-ruthenium catalyst. The ruthenium is in the form of the free-metal.

Zeolite Group VIII metal catalysts have also been reported as useful in refinery operations. The ruthenium is generally reduced or modified by other means such as by reaction with $H_2S$.

SUMMARY

It has now been found that zeolite supported ruthenium catalysts in which the ruthenium is still in a cantionic form are very effective hydrogenation catalysts.

DESCRIPTION OF THE PREFERRED EMBODIMENT

A preferred embodiment of the invention is a hydrogenation process comprising contacting an organic material susceptible to hydrogenation with hydrogen in contact with a catalyst consisting essentially of zeolite support containing a catalytic amount of ruthenium in cationic form.

The process can be used to hydrogenate a broad range of organic compounds such as ketones (e.g. acetone, methylethyl ketone, cyclohexanone, and the like), unsaturated heterocyclic compounds (e.g. furan derivatives), olefins (e.g. hexene-1, cyclohexene, cyclooctene, and the like), aromatics (e.g. benzene, toluene, xylene, naphthalene, benzyl alcohol, and the like).

The catalyst can be made using a broad range of zeolites, many of which are available commercially. Zeolite A is described in U.S. Pat. No. 2,882,243. Zeolite X is described in U.S. Pat. No. 3,882,244. Zeolite Y is shown in U.S. Pat. No. 3,130,007 and U.S. Pat. No. 3,130,006. Zeolite L is described in U.S. Pat. No. 3,216,789. Zeolite structure is discussed in D. L. Breck, "Zeolite Molecular Sieves", J. Wiley and Sons, N.Y. 1974. Zeolites are reviewed in an article by J. Turkevich, "Catalytic Reviews", 1, pp. 1–35 (1967). Zeolite SK-89 is available from Linde Division of Union Carbide Corp. Zeolite ZK-4 is described in U.S. Pat. No. 3,314,752. Partial replacement of sodium cation with calcium is described in U.S. Pat. No. 2,306,610. Complete replacement with calcium is taught in U.S. Pat. No. 2,522,426. Zeolite ZK-20 is described in U.S. Pat. No. 3,459,676.

The catalysts can be readily made by impregnating a zeolite with an aqueous solution of a water soluble ruthenium salt. Following this the catalyst is oven dried and usually ground to a powder form prior to use. The catalyst contains about 0.01–10.0 weight percent ruthenium. The catalyst is not reduced prior to use and use conditions are such that the ruthenium remains in cationic form. The catalyst has the advantage that is not easily poisoned and can be reused many times with any further treatment. The following examples shows a method for making the zeolite catalyst containing ruthenium cation.

EXAMPLE 1

Catalyst Preparation

To 1500 ml of $H_2O$ was added 16.0 g. of $RuCl_3$ 1-3 $H_2O$. Slowly to this solution was added 160 g. of LZ-y52 zeolite and allowed to stir until aqueous solution is clear (usually 1-3 hours). This is a crystalline sodium alumino-silicate molecular sieve having a 24.68 angstrom unit cell. It can be obtained from Linde Division of Union Carbide Corporation. The catalyst was then filtered off, washed once with an equal volume (1500 ml) of $H_2O$ and dried in an oven at 90° C. The catalyst was powdered and used in the unreduced cationic form.

Organic compounds of hydrogenation are readily hydrogenated by placing them in an autoclave together with the present catalyst. Good results can be achieved using an amount of catalyst equal to about 0.5–15 weight percent of the reaction mixture including solvents. Useful solvents include alcohols such as methyl alcohol, ethanol, isopropanol and the like. The following examples show the process of hydrogenating various organic compounds using the zeolite-ruthenium cation catalyst.

EXAMPLE 2

Reduction of Aliphatic Ketone

Into a 300 ml stainless steel stirred autoclave was charged 118.5 g. (150 ml) of acetone and 2 g. (5 percent by weight) of the ruthenium zeolite. The system was pressurized with hydrogen and heated to 50° C. to initiate rapid reduction. After 33 percent of the theoretical uptake (based on the ideal gas law) of $H_2$ was complete (20 min.), the reaction was cooled, catalyst filtered off and products analyzed.

Gas chromatographic analysis gave an isopropanol product yield of 27.5 percent with the remaining 72.5 percent as unreduced acetone.

EXAMPLE 3

Reduction of Cycloaliphatic Ketone

To a 300 ml stainless steel autoclave was charged 11.5 g. of 4-methylcyclohexanone in 100 ml methanol with 1 g. of 5 percent by weight cationic ruthenium zeolite. After pressurizing with hydrogen to 1450 psig, the system was heated to 55° C. to initiate rapid uptake. After 7 minutes, the reaction was cooled and product analyzed. Gas Chromatographic analysis indicated 95 percent of 4-methyl cyclohexanol (mixture of isomers) and the remaining 5 percent was identified as the dimethyl ketal (formed due to acidic surface nature of zeolite).

EXAMPLE 4

Reduction of Mononuclear Heteroaromatic Derivative

Into a 300 ml stainless steel autoclave was charged 40.03 g. 2,5-bis-(hydroxymethyl)furan, 100 ml methanol and 3 g. of cationic ruthenium zeolite. After pressurizing with $H_2$ to 1900 psig and initiating stirring, the exothermic reduction occurred increasing the temperature from 30° C. (reaction temperature) to 61° C. The reduction temperature started to decrease as the reduction slowed down. The reduction was complete in 30 minutes and workup gave 99 percent 2,5-bis-hydroxymethyl tetrahydrofuran as the sole product (verified by analysis).

EXAMPLE 5

Scale-up Reduction of Mononuclear Heteroaromatic Derivative

To a 2 gal. stainless steel stirred autoclave was charged 1420.5 g. of 2,5-dihydroxymethylfuran and 113.68 g. of the cationic ruthenium zeolite and 1 gal. of methanol. The system was pressurized with $H_2$ to 3500 psig and heated to 30° C. An exothermic gas uptake was seen and the temperature rose within a minute to 82° C. Cooling water was started to control the exothermic reaction. After 5 hours, gas uptake had essentially ceased and gas chromatographic analysis indicated no starting material was present. Distillation gave 92 percent yield of 2,5-dihydroxymethyl tetrahydrofuran and about 8 percent of a product identified as 5-methyl tetrahydrofuran-2-methanol (hydrogenolysis product).

EXAMPLE 6

Reduction of Mononuclear Heteroaromatic Derivative

To a 300 ml autoclave was charged 21.39 g. of furfuryl alcohol, 2 g. of the cationic ruthenium zeolite and 100 ml of methanol. The reaction was pressurized to 1850 psig with $H_2$ and heated to 45° C. The reaction was complete in 30 minutes. The product was tetrahydrofurfuryl alcohol in 100 percent yield (G.C. yield).

EXAMPLE 7

Reduction of Mononuclear Aromatic Derivative

In a 300 ml stainless steel autoclave was charged 20.3 g. benzyl alcohol, 100 ml methanol and 2 g. of the cationic ruthenium zeolite. The reaction vessel was pressurized with $H_2$ to 1500 psig, heated to 45° C. and alllowed to stir for 12 hours. After cooling, G.C. analysis indicated 100 percent cyclohexylmethyl alcohol as the sole product.

EXAMPLE 8

Reduction of Dinuclear Heteroaromatic Benzene Derivative

To a 300 ml stainless steel autoclave was charged 20.3 g. quinoline, 100 ml methanol and 2 g. of the cationic ruthenium zeolite. The reaction vessel was pressurized with $H_2$ to 2070 psig, and heated to 57° C. Gas uptake was very rapid over the first hour and then the rate slowed down. Reaction was allowed to run for 16 hours. Workup and analysis by Gas Chromatography and mass spectral data gave 49.1 percent of the decahydroquinoline, 1.6 percent of the 5,6,7,8-tetrahydroquinoline and 49.3 percent of 1,2,3,4-tetrahydroquinoline.

EXAMPLE 9

Reduction of Carbocyclic Olefin

To a 300 ml stainless steel autoclave was charged 113.20 g. cyclohexene and 2 g. of the cationic ruthenium zeolite. The vessel was pressurized with $H_2$ to 2000 psig and stirring started. The reduction started immediately and the heat of reaction increased the temperature from 20.1° C. to 169° C. Cooling was started to control the reaction. Reduction was complete in 8 minutes. Workup and analysis shows cyclohexane as the sole product in 100 percent yield.

EXAMPLE 10

Reduction of Heterocarbocyclic Olefin

To a 300 ml autoclave was charged 131.3 g. of dihydropyran and 2 g. of the cationic ruthenium zeolite. The vessel was pressurized with $H_2$ to 2100 psig and stirring started. The reduction started immediately and the heat of reduction increased the temperature from 30.8° C. to 131.0° C. Cooling was applied to control the exothermic reaction. Reduction was complete in 4 minutes. Workup and analysis indicated that pyran was the sole product in 89 percent yield with 11 percent unreduced dihydropyran remaining.

The reduction are well-known chemicals and have established utility. For, example, tetrahydrofurfuryl alcohol can be used for the preparation of dihydropyran, as an industrial solvent, or as an intermediate in the preparation of 1,5-pentanediol useful in polyurethane manufacture.

I claim:

1. A hydrogenation process comprising contacting an organic material susceptible to hydrogenation with hydrogen in contact with a catalyst consisting essentially of zeolite support containing a catalytic amount of ruthenium in cationic form and under temperature and pressure conditions such that said ruthenium remains in cationic form.

2. A process of claim 1 wherein said organic material is a ketone wherein the carbonyl group is reduced to a carbinol.

3. A process of claim 1 wherein said organic material contains a furan ring wherein the furan ring is reduced to a tetrahydrofuran group.

4. A process of claim 1 wherein said organic material contains a benzene ring wherein said benzene ring is reduced to a cyclohexyl group.

5. A process of claim 1 wherein said organic material contains an olefinic double bond wherein said double bond is hydrogenated.

* * * * *

UNITED STATES PATENT AND TRADEMARK OFFICE
CERTIFICATE OF CORRECTION

PATENT NO. : 4,459,419

DATED : JULY 10, 1984

INVENTOR(S) : PAUL D. SEEMUTH

It is certified that error appears in the above-identified patent and that said Letters Patent is hereby corrected as shown below:

Column 2, line 15, reads "Organic compounds of" and should read -- Organic compounds capable of --.

Column 3, line 34, reads "45°C and alllowed" and should read -- 45°C and allowed --.

Column 4, line 27, reads "The reduction are" and should read -- The reduction products are --.

Signed and Sealed this

Eleventh Day of December 1984

[SEAL]

Attest:

GERALD J. MOSSINGHOFF

Attesting Officer     Commissioner of Patents and Trademarks